(12) United States Patent
Noble et al.

(10) Patent No.: US 10,605,758 B2
(45) Date of Patent: Mar. 31, 2020

(54) DEVICES AND METHODS FOR TESTING ANALYTES

(71) Applicant: EXACSYS LIMITED, London (GB)

(72) Inventors: Michael Noble, Melbourn (GB); Craig Nelson, Melbourn (GB); Mark Humphries, Melbourn (GB); Carys Lloyd, Melbourn (GB); David Edington, Melbourn (GB); John Rippeth, Melbourn (GB)

(73) Assignee: PA Knowledge Limited, London (GB)

( * ) Notice: Subject to any disclaimer, the term of this patent is extended or adjusted under 35 U.S.C. 154(b) by 62 days.

(21) Appl. No.: 15/151,004

(22) Filed: May 10, 2016

(65) Prior Publication Data

US 2016/0252477 A1    Sep. 1, 2016

Related U.S. Application Data

(62) Division of application No. 13/696,380, filed as application No. PCT/GB2011/000703 on May 6, 2011, now abandoned.

(30) Foreign Application Priority Data

May 7, 2010   (GB) .................................... 1007711.3

(51) Int. Cl.
   *G01N 27/327*     (2006.01)
   *G01N 33/49*      (2006.01)
   (Continued)

(52) U.S. Cl.
   CPC ......... *G01N 27/3272* (2013.01); *C12Q 1/006* (2013.01); *C12Q 1/54* (2013.01);
   (Continued)

(58) Field of Classification Search
   None
   See application file for complete search history.

(56) References Cited

U.S. PATENT DOCUMENTS 6,830,669 B2    12/2004   Miyazaki et al.
7,022,219 B2 *   4/2006   Mansouri ............. G01N 33/492
                                                          204/401
(Continued)

FOREIGN PATENT DOCUMENTS

CN    101598702    12/2009
CN    101614746    12/2009
(Continued)

OTHER PUBLICATIONS

Trividia Control Solution FAQ, accessed Mar. 13, 2014.*
(Continued)

*Primary Examiner* — Gurpreet Kaur
*Assistant Examiner* — Steven E Rosenwald
(74) *Attorney, Agent, or Firm* — Nixon & Vanderhye P.C.

(57) ABSTRACT

A method and device are provided for measuring a level of a clinically relevant analyte (such as glucose) in a fluid (such as blood). The device includes a flow path for conducting said fluid through the device; a detection chamber arranged on said flow path; and detector means arranged to detect analyte levels in the fluid in said chamber, wherein: said detection chamber contains a predetermined amount of an analyte such that that analyte mixes with fluid in the detection chamber to form, at the detector means, a calibration sample of the fluid at a time after the arrival of the fluid in said detection chamber, and said detector means is arranged to detect a first analyte level of an unadulterated sample of the fluid at a first time which is before the formation of said calibration sample and to detect a second analyte level of (Continued)

Figure 1A:
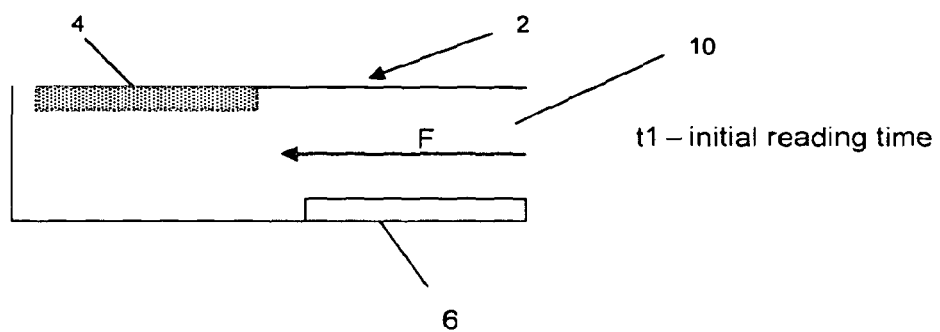

said calibration sample at a second time which is after the formation of said calibration sample.

13 Claims, 3 Drawing Sheets

(51) Int. Cl.
*C12Q 1/00* (2006.01)
*C12Q 1/54* (2006.01)

(52) U.S. Cl.
CPC ..... *G01N 27/3271* (2013.01); *G01N 27/3274* (2013.01); *G01N 33/4915* (2013.01); *G01N 33/49* (2013.01); *G01N 2496/00* (2013.01)

(56) References Cited

U.S. PATENT DOCUMENTS

| | | |
|---|---|---|
| 2005/0139469 A1 | 6/2005 | Davies et al. |
| 2006/0024835 A1 | 2/2006 | Matzinger et al. |
| 2007/0202606 A1 | 8/2007 | Noble |
| 2007/0287191 A1 | 12/2007 | Stiene |
| 2008/0179197 A1 | 7/2008 | Wu |
| 2009/0101498 A1* | 4/2009 | Papadimitrakopoulos ............ C12Q 1/006 204/403.11 |
| 2009/0112420 A1 | 4/2009 | Buur et al. |
| 2009/0192366 A1 | 7/2009 | Mensinger et al. |
| 2013/0068633 A1 | 3/2013 | Chatelier et al. |
| 2013/0112573 A1 | 5/2013 | Noble et al. |

FOREIGN PATENT DOCUMENTS

| | | | |
|---|---|---|---|
| EP | 1621887 A1 * | 1/2006 | ........... G01N 33/487 |
| EP | 1 621 887 | 2/2006 | |
| JP | 2004233294 * | 8/2004 | ............. G01N 27/26 |
| WO | WO 2005/080970 | 9/2005 | |
| WO | WO 2005/080970 A1 * | 9/2005 | ........... G01N 33/487 |
| WO | WO 2007/040913 | 4/2007 | |
| WO | WO 2008/029110 | 3/2008 | |
| WO | WO 2008/029110 A2 * | 3/2008 | ........... G01N 27/327 |
| WO | WO 2011/012848 | 2/2011 | |
| WO | WO 2011/012848 A1 * | 2/2011 | ............... C12Q 1/00 |

OTHER PUBLICATIONS

Chinese Office Action and Search Report dated Feb. 20, 2014, issued in connection with Chinese Patent Application No. 201180033551.2 and English translation of Chinese Search Report.
"Arkles (Oct. 2006 issue of Paint & Coatings Industry magazine), "Hydrophobicity, Hydrophilicity and Silanes", 10 pages (in U.S. Appl. No. 13/696,380 ("Devices and Methods for Testing Analytes" Nobel et al.) as Part of Paper No. 20150312)".
International Search Report for PCT/GB2011/000703, dated Nov. 7, 2011, C.F. Angioni.

* cited by examiner

DEVICES AND METHODS FOR TESTING ANALYTES

This application is a divisional of application Ser. No. 13/696,380 (pending), filed Jan. 11, 2013 (published as US 2013-0112573 A1), which is the U.S. national phase of International Application No. PCT/GB2011/000703, filed 6 May 2011, which designated the U.S. and claims priority to GB Application No. 1007711.3, filed 7 May 2010, the entire contents of each of which are hereby incorporated by reference.

The present invention relates to devices and methods for testing clinically relevant analytes in samples of biological origin. It is particularly, but not exclusively concerned with methods and devices with improved accuracy for testing blood glucose levels.

Examples of clinically relevant analytes are indicators of cardiovascular, liver and kidney function (e.g. cholesterol, haemoglobin, electrolytes, metabolites), infectious agents (e.g. viruses, bacteria), disease state indicators (e.g. C-reactive protein, antibodies, cellular signalling factors, hormones) and therapeutic agents (e.g drugs) and in particular glucose. Examples of samples of biological origin include cerebrospinal fluid, urine, semen, saliva and in particular whole and fractionated blood.

In recent years, there has been growth in the number and types of clinical diagnostic tests carried out outside of the traditional laboratory setting. Many test systems have been developed and marketed for use at the "Point of Care" ("POC"), including systems which are used at hospital bedsides, in intensive care units, in the offices of doctors or physicians and in the patient's home or at other locations which are desirable or convenient.

In some instances these tests may be carried out by healthcare professionals (although not necessarily trained laboratory staff) but in others the patients themselves conduct the testing to help monitor and manage their own condition. The most common self testing systems are for blood glucose monitoring ("BGM") in patients with diabetes, but other tests, such as blood coagulation time testing for patients undergoing Warfarin therapy, are also becoming more common.

In particular the management of diabetes has been considerably improved by the availability and use of self-testing Blood Glucose Monitoring (BGM) systems. These systems allow diabetics to determine their own blood glucose levels and, depending on the result, to adjust their therapy or modify their diet, thus maintaining their glucose levels within a relatively narrow band within what is considered to be a healthy level.

This ability for diabetics to test and consequently control their own blood glucose levels tends to result in a lower incidence of diabetes related complications, as evidenced by the 1993 Diabetes Control and Complications Trial (DCCT, New England Journal of Medicine 329 (14), Sep. 30, 1993).

In addition to the difference in the training and experience of the person conducting clinical diagnostic tests from a trained laboratory technician to a more generalised healthcare practitioner or patient, there are a number of other key differences between POC tests and lab-based tests. These include the relatively uncontrolled (and therefore variable) testing conditions in the POC setting (e.g. ambient temperature and humidity), a lower level of control of the storage conditions and consequential ageing of diagnostic chemistries and variations in the biological sample matrix for the analyte under test. Mass produced POC test systems generally do not take these variabilities into account when interpreting readings and providing results.

Moreover, the very high number of tests that can be carried out in the POC setting (several billion BGM test strips are used every year) means that manufacturing methods have to be very well controlled to maintain consistency of readings and results both within and between batches.

Each of these factors can individually cause error in the diagnostic performance of a POC test system, thereby undermining the advantages that this mode of testing can offer.

For example, the accuracy of the blood glucose readings generated by existing BGM systems (which typically use an enzyme electrode where an enzyme such as glucose oxidase or glucose dehydrogenase catalyses the reaction of glucose producing an electrically measurable signal, potentially via use of an electrochemical redox mediator) can be adversely affected by a number of factors, such as:

1. Variability in hematocrit level of test blood. Since BGMs are generally designed to function in a diffusion limited manner, where the signal is dependent on the flux of glucose molecules to the sensor surface which is in turn related to the bulk concentration, then variability in the diffusive properties of the sample matrix can lead to testing inaccuracy. In blood, this effect is most apparent with variable hematocrit levels, where, for instance, at higher than normal levels the presence of a greater concentration of red blood cells can impede diffusion, slowing flux of the analyte to the electrode surface.
2. Variation in the prevailing environmental conditions during testing. BGM systems are sensitive to the temperature at which testing is being conducted since temperature affects both enzyme kinetics and diffusion rates. Additionally, altitude can have an impact since it may affect the oxygen availability at the electrode surface-oxygen is required in GOD-catalysed reactions in certain electrode configurations, but can also impede the overall reaction rate by competing with redox mediators in alternative configurations.
3. Instability of the reaction components—particularly the enzymes used in the detectors which may be subject to a change of activity due to temperature and/or humidity effects over the storage time. Electrochemical redox mediators used in some systems can have similar environmental sensitivity thus providing a further contribution to error from an environmental source.
4. Lack of specificity of the enzyme—whilst GOD is a highly specific enzyme with limited capability to catalyse the oxidation of molecular species other than glucose, enzyme electrodes based on other enzymes can be less specific. For example, certain glucose dehydrogenase (GDH) based systems with the redox mediator pyrroloquinoline quinine (PQQ) are known to cross react with other sugars such as maltose, galactose and xylose and since these substances may be found in certain drug and biologic formulations, this can lead to a falsely high 'glucose' reading.
5, The presence of interfering substances in the patient's blood—some substances such as acetaminophen and ascorbate are electroactive and can themselves generate an electrical signal on being oxidised at an electrode surface
6. Manufacturing process variation—strips are manufactured in large batches and a calibration is determined for each batch to enable conversion of the electrical signal into a blood glucose reading. The calibration set for a particular batch reflects the average performance of the strips in terms of their electrical response to blood glucose over the range of clinically feasible values. However, for any one particular strip, it is likely that it will deviate from the average and so the 'batch calibration' applied to the signal generated by that strip will not provide an accurate reading of the blood glucose concentration in the sample.

7. Inappropriate calibration—strip batches are typically calibrated for their response to blood glucose and each manufactured batch has a 'calibration code' that enables the meter to convert electrochemical readings into glucose concentrations. Because there is variation between batches, calibration codes may differ. Inaccuracy may therefore arise if a meter is using a calibration code that is inappropriate for the batch of strips being used in testing.

8. Improper testing procedure—modern BGM systems are designed to reduce the likelihood of improper testing procedure, or 'user error'. However, there is a possibility that BGM systems will be used outside of their specified conditions of, for instance, temperature or altitude. Equally, users might inadvertently affect the accuracy of their blood glucose readings by improper preparation of the blood test site, for example by insufficient drying of wet hands leading to a diluted blood sample.

Whilst these error sources have been described with electrochemical detection of enzyme generated electroactive species, similar errors can occur with optical and spectral detection systems.

As a result of these and other sources of error, commercially available BGM systems typically have system accuracy levels (also known as total error) of up to 20%, compared to a reference laboratory method.

Over the years since introduction of self monitoring of blood glucose there have been calls for tighter accuracy standards from bodies such as the American Diabetic Association (ADA). For example in 1993 a consensus statement was issued recommending an accuracy target of ±5% for BGM systems. More recently, the FDA has indicated that it is unhappy with the current ±20% accuracy standard (for 95% of readings) and has stated that it may consider recognising a higher performance standard in future.

Examples of known BGM devices and disadvantages associated with them are discussed in the introductory portion of WO2005/080970, the contents of which are hereby incorporated by reference.

Whilst the above discussion has focussed primarily on BGM systems, similar problems are experienced with devices and methods for measuring other clinically relevant analytes.

In order to improve system accuracy, current approaches are focussed on the recognised sources of error in POC tests.

For example, error arising from manufacturing imprecision can be addressed by improving the manufacturing process control and, potentially, investing in new manufacturing technologies such as advanced printing or laser ablation techniques.

Attempts minimise the adverse impact of variable environmental conditions such as temperature and altitude are focussed on developing sensing and signal processing mechanisms that modify the raw signal according to an algorithm.

In terms of the presence of interferents, effort is concentrated on development of new chemistries or sensing technologies that are less sensitive to these interferences or the use of selective membranes that can specifically exclude certain interferents from the sensing electrode. Sample effects, such as variable hematocrit, are often corrected for by electrochemical systems that measure the extent of these effects and make a correction accordingly.

Finally, attempts to reduce the likelihood of user error include the development of systems where the user intervention is more controlled, for instance by controlling blood introduction into the strip by the use of a capillary fill method.

Each of these approaches requires significant investment in terms of time and money. Moreover, the system accuracy improvement from these approaches can be limited, since each approach typically addresses only a limited number of sources of error.

AgaMatrix has developed a method (described in US2009/166225) of correcting an analyte-dependent signal by using an analyte-independent signal. This method may require complex sensors and associated signal processing capabilities and require longer test times to allow for the collection of sufficient data features to enable a correction to be made.

Nova Biomedical has developed a BGM system, the Stat Strip, which utilises a series of measurement wells to measure electroactive interferences and haematocrit independently of the analyte glucose (US6237451). This information is used to correct the measured giuco signal and thereby aims to provide a more accurate reading.

Such methods of measuring an analyte independent signal may have relatively low sensitivity because the analyte independent signal and the analyte dependent signal are measured under the same test conditions, which are usually optimised for the analyte dependent signal measurement. Accordingly, the low sensitivity of analyte independent signal measurements affords only limited ability to correct the analyte dependent signal.

Despite the application of many methods to reduce BGM system error, there still remains significant inaccuracy in BGM systems marketed today. Error caused by variability in the hematocrit level of the test sample and the test temperature are currently amongst the most significant remaining sources that have not been adequately addressed.

WO2005/080970, referred to above, discloses a method for improving the accuracy of POC test devices (including BGM devices) by adding a predetermined amount of analyte to be tested to the test sample and comparing the resultant signal with that from an unadulterated sample. This method enables a correction to be made to the unadulterated sample reading based on the readings in the sample(s) with analyte added. In effect this enables an element of 'live', (or 'on rip') calibration and aims to minimise or eliminate testing error from resulting from many error sources including enzyme electrode instability, sample effects (such as haematocrit level), improper test procedure (such as inappropriate temperature), inappropriate calibration code and manufacturing imprecision.

The devices and methods set out in WO2005/0B0970 generally rely on calibration by spatial separation of the unadulterated and calibration samples (either to use separate detectors or separate flow paths to a common detector).

The present invention seeks to provide devices and methods which have improved accuracy and remain simple and cheap to manufacture.

It is a further object of the present invention to provide methods of calibration which are compatible with existing devices without significant alteration of those devices, and devices which can be manufactured using essentially existing production processes.

At its broadest the present invention provides methods and devices for measuring levels of clinically relevant analytes, such as glucose, in a fluid and calibrating that measurement as a result of measurement of a calibration sample within the same device.

At its broadest a first aspect of the present invention provides a method for measuring levels of clinically relevant analytes, such as glucose, in a fluid and calibrating that measurement as a result of subsequent measurement of a calibration sample by the same detector.

A first aspect of the present invention provides a method for testing, in a portable device, a level of a clinically relevant analyte in a fluid, the method including the steps of: guiding a sample of the fluid to a detection chamber containing a predetermined amount of an analyte; measuring an analyte level in an unadulterated sample of the fluid at a first predetermined time after the arrival of the fluid in said detection chamber; measuring an analyte level in a calibration sample of the fluid which has mixed (either completely or in part) with said predetermined amount of said analyte at a second predetermined time after the arrival of the fluid in said detection chamber, being later than said first predetermined time; and adjusting the analyte level measured in said unadulterated sample using the analyte level measured in said calibration sample.

Any of the following optional features (including combinations of some or all such features) may be included in the method of this first aspect.

The detection chamber may form part of the flow path or be a separate chamber connected to the flow path.

In one embodiment said analyte in said predetermined amount of analyte is the same as said clinically relevant analyte. As a result the measurement means both for the unadulterated sample and the calibration sample can be the same, and so errors that affect the measurement means can be detected and adjusted for.

As both the unadulterated sample and the calibration sample are present or formed in the detection chamber, they can both be measured by a single detector. Thus there is a temporal separation between the measurement of the unadulterated sample and the measurement of the calibration sample and any errors due to variation in the detectors used for measuring the levels in the calibration and unadulterated samples can be avoided.

Furthermore, as both the unadulterated sample and the calibration sample are formed from the same volume of fluid, there is no requirement for an additional amount of fluid to be provided for the analysis.

In alternative embodiments, the calibration analyte may be a different chemical species to the clinically relevant (target) analyte. In one such arrangement the calibration analyte is measurable by part of the overall measurement means used for the target analyte. For example, the calibration analyte might be detected directly at the electrode by electrochemical oxidation under the same, or different, conditions as those used for the target analyte. This arrangement could enable inferences to be made about sub-components of the target analyte measurement (for example, the test temperature affecting the calibration analyte diffusion rate and the electrode dimensions), and allow corrections to the target analyte concentration accordingly. In certain configurations, the use of a calibration analyte of a different chemical species may be advantageous as the different species will not interfere with the target analyte measurement, or will interfere to a lesser extent than if the clinically relevant analyte is also used as the calibration analyte. Alternatively, the calibration analyte could have a particular sensitivity to a component or variable of the test sample that is known to cause erroneous readings.

In certain embodiments, measurement of the calibration sample formed is substantially insensitive to the amount of said predetermined analyte which is present. For example, the step of adjusting may use the rate of diffusion or the time taken to detect the effects of the mixing of the predetermined amount of analyte, or a combination thereof, to adjust the analyte level measured in said unadulterated sample.

In further alternative embodiments, the analyte and calibration measurements may be carried out under different regimes. In one such arrangement there may be a separate detector means where the second (or further) calibration measurements are optimised for measuring an analyte independent signal, in contrast to the primary detector which is optimised for measuring the level of the target analyte. For example the separate detector means may be overlaid with the same reagent (s) as used for the primary detector means except without the addition of an electrochemical mediator. Such mediators may be advantageous in measurement of the target analyte, but can interfere with the measurement of analyte independent signals, such as the electrical resistance change caused by varying hematocrit levels. In other arrangements, it is possible that the two measurement regimes could be established at the same detector, where the reaction conditions change over time. For example, a first measurement of hematocrit could be made at the detector before diffusion of the electrochemical redox mediator to the detector, after which point the detector means is optimised, and used for, target analyte measurement.

By providing 'live' calibration of every sample tested, at the point, of use, potential variations in the test result arising from sample effects (such as the presence of interferences, haematocrit level differences, etc.), environmental factors and manufacturing imprecision can be determined and the test results adjusted accordingly.

Therefore errors in the test results can be substantially reduced, or even effectively eliminated.

The calibration may be applied to the unprocessed measurement of the analyte level in the unadulterated sample and an analyte level reading then generated from the adjusted analyte level.

Alternatively, the internal calibration may be applied to an analyte level reading generated from the measured analyte level in the unadulterated sample, thereby correcting it.

Preferably the clinically relevant analyte is glucose.

Typically the fluid is whole or fractionated blood.

The method of the present invention may allow the weighting given to the 'batch calibration' of sensor strips in the calculation of analyte levels (e.g. blood glucose concentrations) to be reduced as the 'live calibration' weighting is increased. The batch calibration procedure is generally a lengthy and costly process. Therefore use of live calibration according to the present invention could allow the amount of batch testing carried out to be reduced thus saving manufacturing cost.

The analyte level reading may be generated by applying a calibration curve to the analyte level. For example, in the methods of the present invention, analyte levels (such as blood glucose concentrations) may be derived from an electrical signal generated by the sensing chemistry by reference to a calibration curve which relates analyte concentration to signal magnitude. Such 'batch calibration' curves can be generated based on average performance for a batch of strips and do not therefore take into account any particular error related to the individual measurement being made. The method of the present aspect may allow adjustment of the calculated analyte concentration for the unadulterated sample by taking into account the calculated analyte concentration or the kinetics of the change in analyte level in the calibration sample. By such a calibration method, errors relating to the individual measurement being made can be minimised.

In particular embodiments of the methods of the present invention, analyte level readings may be generated by applying a calibration curve to an unprocessed measured analyte level or to an adjusted analyte level.

The calibration curve applied to the unadulterated reading could be different to that applied to the adulterated reading, reflecting for example a difference in signal response over time. Additionally, several measurements of the adulterated sample reading could be taken to establish the kinetics of the dissolution and diffusion of added analyte to the detector. Information relating to the sample matrix (for example its temperature or rheological characteristics) could be inferred from the kinetic profile and this information used to adjust the unadulterated reading by making reference to a known relationship between the sample matrix properties and analytical accuracy effects. This may be achieved by measuring a single parameter of the kinetic profile to provide adjustment for all error sources; or where multiple curve parameters are integrated to provide adjustment for all error sources; or where different curve features provide different adjustments for different error sources.

Preferably the method further includes the step of measuring the analyte level in one or more further calibration samples of said fluid at further predetermined times which are later than said second predetermined time, and the step of adjusting uses all measured analyte levels to calibrate the reading from the unadulterated sample. The further measurements may be carried out in a regular time series (i.e. with a standard interval between measurements).

By taking readings of the calibration samples at more than one point in time, it may be possible to further enhance the accuracy of the calibrated reading.

In addition to providing an improvement in accuracy by adjusting an erroneous measurement, the added analyte response could be used to determine that a measurement is so inaccurate that adjustment should not be made and an error reading is generated, rather than an adjusted reading.

A further potential application of this aspect is to determine the condition of a diagnostic test consumable that may be subject to manufacturing variability or changes due to ageing. In this application, a sample containing a known amount (which may be zero) of the analyte is introduced into the detection chamber.

This may be achieved by effectively "testing" a standardised sample containing a known amount of target analyte in a well characterised sample matrix ('a standard' or 'control solution') using the method of this aspect (optionally in the device of the third or fourth aspects below) and obtaining two signals: one from the unadulterated standard and the other from the adulterated standard sample containing added analyte. This test generates at least two signal readings from a series of predicted analyte concentrations and allows a relationship to be established between sample analyte concentration and signal. Such a relationship would reveal the sensitivity of the diagnostic system to sample analyte as well as the predicted response of the system at zero analyte concentration. This latter reading can be used as a measure of diagnostic test quality since it represents the background reading that is related to non analyte specific response. In the case of electrochemical enzyme electrodes using redox mediators, a high background reading can arise from mediator instability. In practical terms this could be a useful way to test the status of a set of diagnostic test consumables.

Where multiple readings from a calibration sample are taken, the step of adjusting may include calculating one or more rates of change of the signal measured, or of the calculated concentration of the analyte. In particular, the step of adjusting may be performed by inferring or measuring a rate of change in the concentration of said analyte in the fluid in the detection chamber.

The method may further include the step of releasing said analyte for mixing with said fluid in said chamber. Examples of ways in which the release of the analyte may be controlled are discussed in more detail in relation to the third or fourth aspects below. The step of releasing may include one or more of the following: applying an electric field to the analyte in the detection chamber; applying radiation (such as infrared radiation) to the analyte in the detection chamber; applying heat to the analyte in the detection chamber; controlled dissolution of a barrier layer; controlled release from a matrix; controlled release from a surface.

The method may further include the step of storing non-analyte specific information from the measurements performed.

In particular, the method may further including the steps of: storing a record, such as an average or historical data, of said non-analyte specific information; updating said record after subsequent measurements; and determining a deviation from said record in a subsequent measurement.

The method may further include the step of, if said deviation is greater than a predetermined amount, alerting the user.

Accordingly, it may be possible to identify clearly erroneous measurements from the non-analyte specific information and therefore alert the user to the fact that even the adjusted analyte level is not a correct reading. This may arise as a result of extremes of temperature exposure during storage before use of the device, or contamination of the test sample. In other situations, such determination of deviation may identify when different users are using the device and therefore different calibration relationships should be used or applied.

The method may further include the steps of: recording said measured analyte levels for a predetermined length of time; analysing the shape of the measured analyte levels over said predetermined length of time; selecting, based on said analysis, a correction algorithm from a plurality of such algorithms, to be used in said step of adjusting.

In particular, the step of analysing the shape of the measured analyte levels may analyse one or more of the following features of the measured analyte levels: peak height, time to peak height, absolute value of the measured parameter, and maximum gradient of transients for different error sources.

It has been found that different sources of error can affect the time-dependent variation of measured analyte levels in different ways. By analysing the shape of the measured analyte levels over a predetermined length of time it may therefore be possible to determine the most likely or dominant source(s) of error and apply appropriate correction in the adjustment step.

The methods of the present invention preferably also include the step of introducing said fluid to a flow path, wherein said fluid flows along the flow path whilst said steps of measuring and mixing are carried out.

A possible algorithm that may be used to calculate an adjusted analyte concentration is:

$$Gl_{adj} = (Gl_{un} \times Q)(Gl_{cal} - Gl_{un})$$

where $Gl_{adj}$, $Gl_{un}$ and $Gl_{cal}$ are respectively the adjusted analyte concentration, the analyte concentration measured in the unadulterated sample of the fluid, and the analyte concentration measured in the calibration sample and Q is the known increase in concentration of analyte in the calibration sample resulting from the addition of a known amount of the analyte to a known volume of sample.

The step of adjusting may include inferring a property of the sample matrix from the observed signal caused by the added analyte, or from an analyte independent measurement made under a different measurement regime, and using this inference to adjust the unadulterated sample reading. Such inference may particularly be derived where a series of measurements have been made, which may allow a property of the sample matrix to be inferred on the basis of the change in the measured levels over that series.

The levels measured may be concentrations of the analyte, and the sample of fluid which is mixed with the predetermined amount of analyte may be of a known volume.

In the methods of the present invention, the step of adjusting may also include making corrections based on one or more external factors such as ambient temperature or altitude. In this respect, 'external' is used to refer to a correction that arises from use of an analyte independent measurement method or system separate from the analyte dependent measurement method or system (for example a temperature reading provided by a thermistor within an associated meter). By incorporating information from such sources with the information derived from the calibration analyte or different measurement regime reading the effect of external conditions (such as environmental conditions) on the measurements can be compensated for.

The method may be carried out using a device according to the third or fourth aspects of the invention below, including some, any or all of the preferred or optional features of that aspect. However, it will be appreciated that other devices may also be used in methods according to the present invention.

A second aspect of the present invention provides a method for testing, in a portable device, a level of a clinically relevant analyte in a fluid, the method including the steps of: guiding a sample of the fluid to a detection chamber containing a predetermined amount of an analyte; measuring an analyte level in an unadulterated sample of the fluid; measuring an analyte level in a calibration sample of the fluid which has mixed (either completely or in part) with said predetermined amount of said analyte; and adjusting the analyte level measured in said unadulterated sample using the analyte level measured in said calibration sample.

The method of this aspect may include any individual optional feature discussed above in relation to the first aspect, or any combination of some or all such features, without limitation to essential features of the first aspect which are not part of this second aspect.

For example, the method of this second aspect may include the step of storing non-analyte specific information from the measurements performed or may include the steps of: recording said measured analyte levels for a predetermined length of time; analysing the shape of the measured analyte levels over said predetermined length of time; and selecting, based on said analysis, a correction algorithm from a plurality of such algorithms, to be used in said step of adjusting.

At its broadest a third aspect of the present invention provides a device for measuring levels of clinically relevant analytes, such as glucose, in a fluid and calibrating that measurement as a result of subsequent measurement of a calibration sample by the same detector.

A third aspect of the present invention provides a device for measuring a level of a clinically relevant analyte in a fluid, including: a flow path for conducting said fluid through the device; a detection chamber arranged on said flow path; and detector means arranged to detect analyte levels in the fluid in said chamber, wherein: said detection chamber contains a predetermined amount of an analyte such that that analyte mixes with fluid in the detection chamber to form, at the detector means, a calibration sample of the fluid at a time (or series of times) after the arrival of the fluid in said detection chamber, and said detector means is arranged to detect a first analyte level of an unadulterated sample of the fluid at a first time which is before the formation of said calibration sample and to detect a second analyte level of said calibration sample at a second time which is after the formation of said calibration sample.

Any of the following optional features (including combinations of some or all such features) may be included in the device of this third aspect.

Preferably the analyte in said predetermined amount is the same as said clinically relevant analyte. As a result the measurement of both the unadulterated sample and the calibration sample can be carried out by the same method, and so errors in that method can be detected and adjusted for. Alternatively a different calibration analyte may be used as described in relation to the method of the first aspect above.

As both the unadulterated sample and the calibration sample are measured in the detection chamber, they can both be measured by a single detector. Thus there is a temporal separation between the measurement of the unadulterated sample and the measurement of the calibration sample and any errors due to variation in the detectors used for measuring the levels in the calibration and unadulterated samples can be avoided.

Furthermore, as both the unadulterated sample and the calibration sample are formed from the same volume of fluid, there is no requirement for an additional amount of fluid to be provided for the analysis.

To simplify the device and keep manufacturing costs low, it is preferable that the device has a single detector means, a single flow path or both.

The use of a single detector and flow path has a number of advantages including the ability to achieve the enhanced accuracy of live calibration without any requirement to increase the required sample volume and size of the device and compatibility of the consumable element with pre-existing meters or reader devices. Moreover, the use of a single detector and sample chamber can eliminate any errors that might arise from differences between detectors and/or dimensions of sample chambers.

Typically the predetermined amount of analyte is provided in solid form and the mixing to form the calibration sample occurs when the analyte dissolves in the fluid.

Preferably the clinically relevant analyte is glucose.

Typically the fluid is blood.

The predetermined amount of analyte in the detection chamber may be arranged in a number of ways which may improve the accuracy of the calibration.

In one arrangement the predetermined amount of analyte is located at a position within the detection chamber remote from the position of the detector means.

For example, the predetermined amount of analyte may be located on an opposing surface of the interior of said chamber to the position of the detector means.

In one configuration, the detector includes a working electrode and said predetermined amount of analyte and the working electrode of the detector are located on opposing surfaces of the detection chamber.

In one arrangement of this configuration, at least part of said predetermined amount of analyte is located directly opposite at least part of said working electrode. In other words, when viewed along an axis perpendicular to the surfaces, the area containing the predetermined amount of analyte and the footprint of the working electrode overlap.

In another arrangement of this configuration, there are two detector means and the distance between said opposing surfaces is different in the region of each of said detector means. This arrangement can allow the rate or time of arrival of analyte at the respective detector means to be different as a result of the different separations.

In this arrangement the diffusion of the predetermined amount of analyte from its position, through the fluid, to the detector means provides sufficient time separation for the detection of the analyte level in the unadulterated sample before subsequent detection of the analyte level in the calibration sample. Typically this time separation is at least 0.1 seconds, preferably at least 0.5 seconds, more preferably at least 1 second. Such time separations have been achieved with distances of at least 100 µm between the detector means and the analyte, but may be achieved with distances of at least 40 µm.

In an alternative or additional arrangement, the chamber has an inlet port connected to said flow path and said predetermined amount of analyte is located at a position in said chamber which is further from said inlet port than the position of said detector means in said chamber. In this arrangement, the additional time taken for the fluid to reach the predetermined amount of analyte after it has already reached the detector means allows a time separation between the measurements.

Additionally, there could be a series of added analyte locations or formulations and the difference between observed and expected added analyte signal could be used to infer information about the test sample matrix that could be used to make a correction to the analyte measurement.

In a further alternative or additional arrangement, the predetermined amount of analyte is contained in a controlled release formulation. Many forms of controlled release formulation are known and can be used for securing the analyte, including (but not limited to) controlled release matrices; multilayer formulations; encapsulation; crystalline structures; or a film coated formulation.

Use of a controlled release formulation may have the same effect as locating the predetermined amount of analyte in a particular position within the detection chamber as it allows control of the time taken for the effects of that predetermined amount of analyte to reach the detector means. The use of a controlled release formulation may, of course, be done in conjunction with specific locations of the analyte.

Controlled release formulations can work in a variety of ways. In some controlled release formulations, the formulation will not release its contents until a certain time after contact with the fluid. This can provide the desired time separation between detection of the analyte levels in the unadulterated and calibration samples.

In other controlled release formulations, the formulation does not release anything until it has been activated. Such activation generally acts to chance the structure of the formulation thereby allowing release. This may be by application of an energy source to either change the temperature of the formulation or to promote mixing.

In one specific arrangement, the controlled release formulation is configured so as to contain the analyte in a number of micelles. The application of an electrical field to the formulation causes the micelles to be disrupted, thereby releasing their payload of analyte. To achieve this the detection chamber may contain one or more electrical elements.

Other activation methods for controlled release formulations include irradiation (for example with infrared light) and heating.

In one arrangement, said predetermined amount of analyte is located on a substrate at a predetermined position in relation to the position of the detector means.

The flow path and detection chamber may be formed by a plurality of structural components and said substrate may form part of at least one of said structural components.

This arrangement allows the predetermined amount of analyte to be located on the substrate which is then incorporated into the device.

In particular arrangements, the substrate may be arranged or manufactured so as to control the location of the analyte on the substrate. For example, the predetermined location of the analyte may be within an area on said substrate which has a different surface energy to other area on the same substrate.

There are a number of ways of providing an area on the substrate with a different surface energy. For example, the predetermined location of the analyte may be in a hydrophilic well which is surrounded by a hydrophobic area. In many cases the analyte will be deposited onto the substrate in solution, in which case the provision of a hydrophilic well within an otherwise hydrophobic area of the substrate will enable precise positioning of the analyte solution, avoiding spreading of the solution across the hydrophilic area.

Alternatively the substrate on which the predetermined amount of analyte is located may be generally hydrophobic and the formulation containing the predetermined amount of analyte may provide a hydrophilic surface that facilitates capillary fill of the flow path and detection chamber.

In another arrangement the substrate on which the predetermined amount of analyte is located is generally hydrophobic and is covered by a layer of hydrophilic material which forms a wall of the flow path. This hydrophilic covering material may be arranged to dissolve on contact with the test sample, exposing the added analyte and allowing it to mix with test sample.

In certain embodiments, the predetermined amount of analyte is contained within a formulation containing a thickening agent such as PVP, OVA, alginate, CMC, HPMC, pullulan etc.

In one embodiment, the predetermined amount of analyte is positioned in a line across the width of the flow path or detection chamber in a direction orthogonal to the direction of flow through the flow path or into the detection chamber.

This arrangement of the analyte allows the device to take account of manufacturing tolerances in the width of the flow path or detection chamber. As an increase or decrease in the width of the flow path of detection chamber will result in an increase or decrease in the volume of fluid in the flow path or detection chamber, positioning the analyte in this manner results in a corresponding, preferably proportional, increase or decrease in the amount of analyte in said predetermined amount.

In other arrangements the flow path and detection chamber are formed by a plurality of structural components and said predetermined amount of analyte is contained within the device on a substrate which is separate from said structural components.

Variation of the formulation of added analyte and factors such as the spatial geometry of the sample chamber, flow patterns, surface energy modification can be applied together to tune the temporal separation of the measurement of unadulterated and adulterated sample such that discrimination between the measurements is optimised in the shortest overall measurement time. In this manner the time separations set out above may be achieved.

In one arrangement, the detection chamber contains 2 or more discrete predetermined amounts of the analyte. Each of these discrete amounts of analyte may be arranged to dissolve into fluid in the detection chamber at a different rate, thereby affecting the concentration profile of the fluid against time after it enters the chamber in a known way. Alternatively or additionally each discrete amount of analyte may be arranged to dissolve into fluid in the detection chamber at a different time, thereby affecting the concentration profile of the fluid against time after it enters the chamber in a known way. In this arrangement, each discrete amount of analyte could be a different chemical species, for example one could be the target analyte and another, the calibration analyte.

The device may further comprise means for applying a variable electrical field to the flow path or to the detection chamber. The variations in electrical field could be used to influence the rates of mixing of components within the calibration sample.

The predetermined amount of analyte may be formulated so that it undergoes an exothermic reaction when dissolving into the fluid to form the calibration sample. This arrangement could quicken rates of mixing within the calibration sample.

The flow path of the device is preferably arranged to reduce propensity for pendant drop formation when said fluid is being added to the device. This can allow the amount of fluid added to the device to be precisely controlled.

In certain embodiments, the device is arranged to accept a precise volume in the detection chamber and has an overflow chamber to accommodate amounts of fluid greater than the capacity of the detection chamber. This allows the quantity of fluid in the detection chamber to be controlled irrespective of the quantity fluid that introduced to the device.

In certain embodiments, said predetermined amount of analyte is formed on a surface of the detection chamber and covered by a further layer, the further layer preventing interaction between the analyte and the fluid and wherein a predetermined area of the analyte is exposed to the interior of the detection chamber by a hole in said further layer. This arrangement has the advantage that the amount of dosed analyte exposed to sample fluid with which it mixes is related to the hole dimensions rather than the total amount of analyte deposited. This may provide for a more precise amount of analyte to be mixed with the sample fluid. Additionally in this arrangement, the analyte is not directly exposed to the flow of the fluid through the flow path and therefore is less likely to be translocated along the flow path as the fluid moves along it. The further layer may be formed from materials which are optimised for causing capillary fill of the flow path.

In certain arrangements, the device includes at least 2 detector means, wherein a first detector means is optimised for measuring the clinically relevant analyte, and a second detector means is optimised for measuring a non-analyte-dependent signal, such that the non-analyte-dependent signal can be used to obtain information about the analyte level measured by the first of said detector means.

In particular, the second detector means may be arranged to detect a quantity related to the diffusivity of the clinically relevant analyte.

In one arrangement, the first detector means includes a redox mediator and the second detector means does not include said redox mediator, and the detector means are arranged such that the measurement of the non-analyte-dependent signal is made before said redox mediator is able to diffuse to the second detector means.

The detector means of the device may be arranged to detect a third (and optionally subsequent) analyte level of additional calibration samples of the fluid at further predetermined times. This can allow a profile of the change in analyte level over time to be recorded and may assist in improving the accuracy of the adjusted reading of the analyte level further.

The detector means of this aspect may include at least one enzyme electrode or other detection means such as optical (absorbance or light scattering based) or spectral (fixed or multiple wavelength based).

The device of this aspect may further include a transducer or processor for processing signals from said detector means to produce an analyte level reading. The analyte level reading may be determined before or after a live addition calibration process is applied, as described in relation to the first aspect above.

Preferably the transducer or processor is adapted to produce an analyte level reading by adjusting the analyte level detected in the unadulterated sample according to analyte level(s) detected in said calibration sample.

Preferably the flow path operates to draw the fluid through the device by capillary action. This may allow the amount of fluid flowing through the device to be known, enabling determination of the increased concentration of analyte in the calibration sample arising from mixing with a known amount of the analyte or may allow the fluid path to be well defined, so that diffusion times of added analyte can be well characterised. This arrangement may also reduce the possibility of user error contributing to an error in the detected analyte levels.

A fourth aspect of the present invention provides a device for measuring a level of a clinically relevant analyte in a fluid, including: a flow path for conducting said fluid through the device; a detection chamber arranged on said flow path; and detector means arranged to detect analyte levels in the fluid in said chamber, wherein: said detection chamber contains a predetermined amount of an analyte such that that analyte mixes with fluid in the detection chamber to form, at the detector means, a calibration sample of the fluid, and said detector means is arranged to detect a first analyte level of an unadulterated sample of the fluid and to detect a second analyte level of said calibration sample.

The device of this aspect may include any individual optional feature discussed above in relation to the third aspect, or any combination of some or all such features, without limitation to essential features of the first aspect which are not part of this fourth aspect.

For example, the device of this second aspect may include at least 2 detector means, wherein a first detector means is optimised for measuring the clinically relevant analyte, and a second detector means is optimised for measuring a non-analyte-dependent signal, such that the non-analyte-dependent signal can be used to obtain information about the analyte level measured by the first of said detector means. Alternatively or additionally the chamber of the device of the second aspect may have an inlet port connected to said flow path and said predetermined amount of analyte is located at a position in said chamber which is further from said inlet port than the position of said detector means in said chamber.

The devices of the present invention may further include one or more sensors, which may be connected to the transducer or processor. The device, for example in the transducer or processor may process signals from the sensor(s) when producing an analyte level reading. The sensors may be, for example, temperature sensors.

The devices of the present invention are preferably portable, and so can be carried by the user and readily available for use in a wide variety of situations.

Figure 1B:
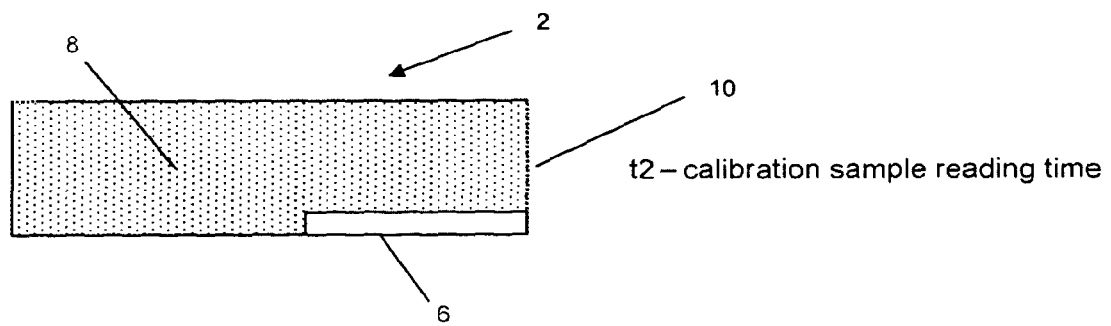
Figure 2A:
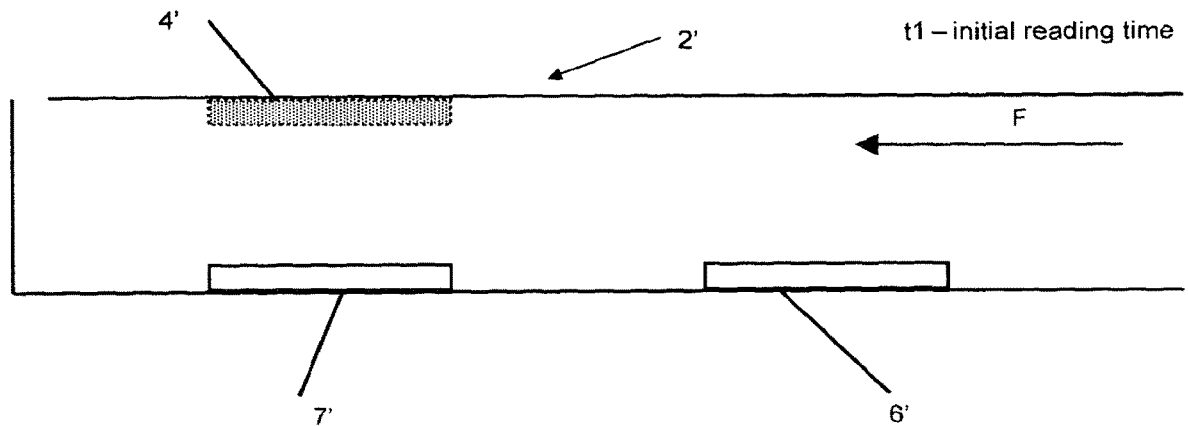
Figure 2B:
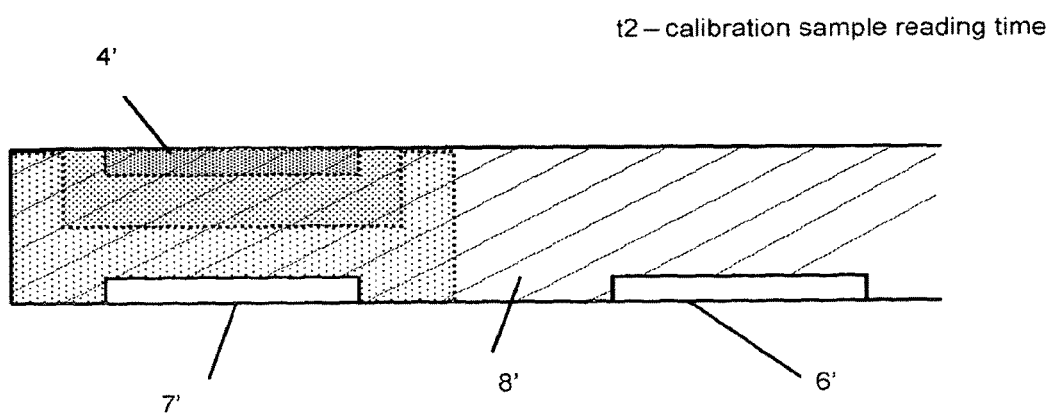
Figure 3A:
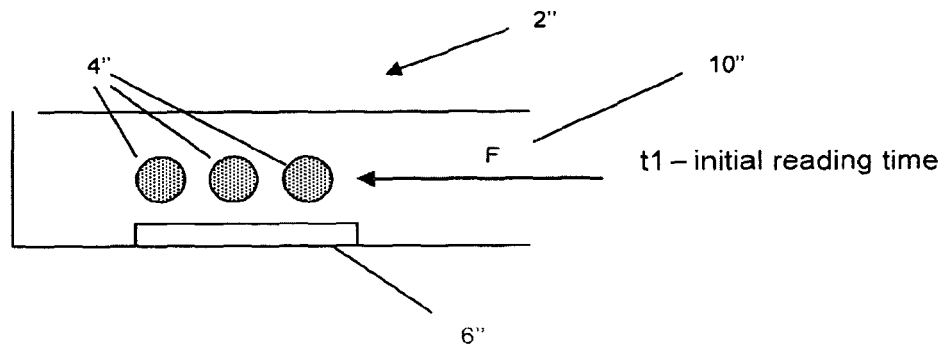
Figure 3B:
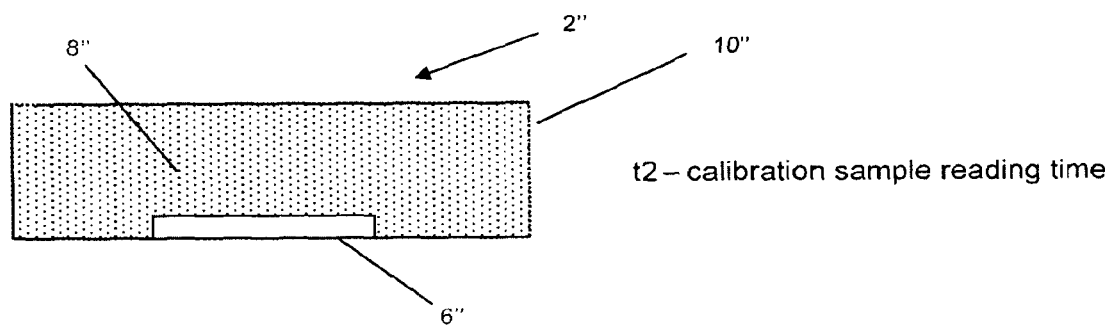

Embodiments of the present invention will now be described with reference to the accompanying drawings, in which:

FIGS. 1A and 1B are schematic illustrations of part of a blood glucose monitoring device according to a first embodiment of the present invention before the flow of blood into the detection chamber and after the additional glucose has been dissolved and diffused;

FIGS. 2A and 2B are schematic illustrations of part of a blood glucose monitoring device according to a second embodiment of the present invention before the flow of blood into the detection chamber and after the additional glucose has been dissolved and diffused; and FIGS. 3A and 3B are schematic illustrations of part of a blood glucose monitoring device according to a third embodiment of the present invention before the flow of blood into the detection chamber and after the additional glucose has been dissolved and diffused to the nearest detector.

A first embodiment of the present invention is shown schematically in FIGS. 1A and 1B. FIGS. 1A and 1B show a detection chamber 2 which is connected to a flow path (not shown) which is arranged to guide the fluid being analysed to the detection chamber 2 via an entry port 10. FIG. 1A shows the chamber 2 before entry of the fluid (as indicated by the arrow F). FIG. 1B shows the chamber 2 after the fluid 8 has filled the chamber 2 and the analyte 4 has dissolved in the fluid 8.

In the embodiment of FIG. 1A the predetermined amount of analyte 4 is provided in the detection chamber 2, and is spatially removed from a detector 6.

The detector 6 is an enzyme electrode such as a glucose oxidase or glucose dehydrogenase based electrode. A standard form of an enzyme electrode is made up of a number of layers. The first is a conductive track, on top of which is the layer containing the enzyme (e.g. glucose oxidase) and, potentially, redox mediators ferricyanide or ferrocene). Above this there may be a mesh which serves to spread out the blood or other fluid being tested. A membrane can also be provided above the electrode surface to physically, chemically or electrically prevent interferents from reaching the enzyme electrode. The detector may include a counter and/or a reference electrode. However, where there is more than one detector, the counter and/or reference electrode may be common between the detectors.

In this embodiment, the time taken for diffusion of the analyte 4 through the fluid 8 being analysed to the detector 6 provides a time window in which the measurement of the unadulterated sample can be made. The second measurement of the calibration sample can be made after a time by which it is known that diffusion of analyte 4 to the detector 6 will have occurred.

As shown in FIG. 1A, the added analyte 4 is situated on the under surface of the lid of the chamber 2 and the detector 6 is situated on the bottom surface of the flow path. The time window between when the detector 6 is measuring an unadulterated sample of the fluid 8 and a calibration sample of the fluid 8 can be adjusted by arranging the position of the added analyte 4 in relation to the entry port 10 and therefore the arrival of the fluid into the chamber. For instance, situating the added analyte 4 "downstream" of the detector 6 (i.e. further from the entry port 10 than the position of the detector 6) as shown in FIG. 1A) allows a first reading to be initiated before the added analyte 4 has been contacted by the fluid entering the chamber 2.

In developments of this embodiment, the detection chamber 2 may contain a number of elements that, together or in isolation, adjust the time window between unadulterated measurement and measurement of calibration sample with added analyte 4 mixed in. For example, the detection chamber 2 may contain one or more microstructural elements (not shown) that promote turbulent flow of the sample fluid in the region of the undissolved additional analyte 4. The presence of these elements would have the effect of enhancing mixing and reducing the time for the added analyte to reach the detector 6. Alternately, turbulence or specific flow patterns could be achieved through modification of the surface energy of different parts of the chamber 2.

It has been found that, for the measurement of glucose in blood, in an arrangement such as that set out in the above first embodiment, it is possible to take a reading of the level of glucose in the blood approximately 0.5 seconds after the arrival of the fluid in the detection chamber which is unaffected by the presence of the additional glucose. A subsequent reading of the level of glucose in the blood can be taken after 5 seconds, by which time some or all of the additional glucose 4 has dissolved in the blood and has also diffused to the detector 6.

FIGS. 2A and 2B show a second embodiment of the present invention. Where components are similar to those shown in the first embodiment above, similar reference numerals are used (e.g. the detection chamber in the two embodiments is denoted by 2 and 2' respectively).

In this embodiment the detection chamber 2' has two detectors 6' and 7'. Both detectors are positioned on the opposite surface of the flow path to the added analyte 4'. Detector 7' is positioned closer to the added analyte 4' than detector 6' so that added analyte diffusing away from its original position after arrival of fluid in the chamber 2' reaches detector 7' first.

By selecting the relative dimensions of the chamber 2' and the positioning of the detectors 6', 7', it is possible to create an arrangement where the detector 7' measures the effect of the added analyte at a time when added analyte has not substantially diffused to detector 6' so that the latter detector measures only the analyte intrinsically present in the unadulterated sample. By this arrangement, both adulterated and unadulaterated sample measurements can be made within the same chamber 2' at the same time, by making use of the separation in distance between the two or more detectors. This configuration is shown schematically in FIG. 2B where the hatched area represents the intrinsic analyte concentration in the fluid 8' and the dotted/stippled areas represent concentrations resulting from dissolution and/or diffusion of the added analyte 4'

It has been found that if detector 7' is positioned opposite added analyte at a distance of less than 200μ, and detector 6' is also arranged on the opposing surface of the flow path but removed in distance along the direction of flow by at least 300μ, separate measurement of adulterated and unadulterated samples is possible within a time window of 1-20 seconds after test sample has filled the capillary. Because the added analyte has not diffused to form a homogeneous concentration of analyte within the entire test sample volume, the measurement of analyte level at detector 7' can be a measure of a transient level (e.g. concentration) or the rate of change of a level.

In an alternative arrangement of this second embodiment the added calibration analyte may be a different species to the target analyte. Both the calibration analyte and the target analyte can be measured at the detector 7'. For example, the calibration analyte could be directly oxidised at the detector producing a signal that would indicate diffusivity of that species in the test sample and this in turn could be used to infer information about the test sample matrix and to adjust the reading of the target analyte level.

Alternatively, the added species could be a substance that inhibits the analyte specific detection reaction. For example, an inhibitor of glucose dehydrogenase or glucose oxidase could be added above the calibration detector in a blood glucose monitoring strip. Inhibition of the glucose specific response at this detector as the substance diffuses to it would allow measurement of the non analyte specific background current that may occur in the presence of electrochemical interferents.

In a further arrangement, based on the second embodiment, one of the detectors 6', 7' could have a different detection chemistry, for example by changing the construction of the detector. For example, the enzyme electrode 6' is arranged to detect the target analyte, but the second electrode 7' may lack components which are present in an enzyme electrode, but which would interfere with a non analyte dependent measurement. For example, a redox mediator may be present as part of the detector 6' but be absent in detector 7'. Because of the diffusion time required to transport any mediator from detector 6' to detector 7', there will be a time window where an electrochemical measurement of a sample property, such as hematocrit level, can be made in the absence of the mediator.

As a result of the absence of the mediator in detector 7° it is possible to make the electrochemical measurement of hematocrit with a high or higher sensitivity than otherwise. This measurement could be used in combination with information derived from the added analyte measurement to accurately adjust the reading of the target analyte level.

This arrangement can therefore provide for a sample parameter specific correction (such as haematocrit), based on the optimised non-analyte dependent measurement, together with a correction based on the measured added analyte specific response—which is indicative of the overall uncorrected detector response to the analyte.

In a further embodiment of this arrangement, it may not be necessary to have an added analyte, since the sensitive non-analyte dependent measurement may provide sufficient opportunity for a substantial correction of the analyte level. This embodiment could be beneficial where the measurement error is substantially attributable to one, or a small defined number of, sample parameters that could be measured by the optimised non-analyte dependent measurement.

In a third embodiment of the present invention, illustrated schematically in FIGS. 3A and 33, the time resolution of the initial and later, adulterated readings is provided by application of specific formulation techniques to the additional analyte. Where components are similar to those shown in the first embodiment above, similar reference numerals are used (e.g. the detection chamber in the two embodiments is denoted by 2 and 2" respectively). Again, FIG. 3A shows the arrangement the detector chamber 2" before entry of the fluid to be tested. FIG. 3B shows the arrangement of the detector chamber 2" after the chamber has filled with fluid and the additional analyte 4" has dissolved in the fluid 8".

In this embodiment, the added analyte 4" and the detector 6" are not significantly spatially separated (in the arrangement shown in FIG. 3A, there is a small separation, but the added analyte 4" could even be formed as part of the detector 6" or located on or around the detector 6"). Instead of the separation of the first embodiment above, the kinetic dissolution or release profile of the added analyte 4" is arranged or chosen such that a first reading can be made before dissolved added analyte 4" is apparent at the detector 6".

This arrangement could be achieved using a range of formulations for the added analyte 4", for example by formulating the analyte 4" in a controlled release matrix (e.g a colloid), in a multilayer formulation, in an encapsulation including a micelle or a liposome based formulation, different crystalline structures, different coating film thickness etc.

One specific way of achieving a controlled release of the analyte 4" of this embodiment is to initiate a change in the structure of the formulation by application of an energy source to either change the temperature or promote mixing. For example, where the analyte 4" is stored in micelles, an electric field applied to the sample at a certain time would cause micelles to be disrupted, thus releasing their payload of analyte. This arrangement could be facilitated by the presence of electrical elements (not shown) within the sample chamber 2". However, other activation methods, such as use of infrared illumination could also be used to activate the formulation.

In this embodiment a plurality of discrete portions of the analyte 4" are provided in the detection chamber 2". The plurality of discrete portions of analyte may be provided to improve the uniformity of the dissolution and diffusion of the analyte in the fluid.

Alternatively, each discrete portion of analyte 4" may be arranged to release its payload of analyte at a different time (for example the nature of the formulation for each portion of analyte may be chosen to achieve a particular release profile, or so that the release of the analyte is triggered by a different source or a different duration in the same environment, or triggered by the release of a component from an earlier release event) thereby creating a known change in the concentration of analyte in the fluid 8" and detected by the detector 6" which can then be used in the calibration of the reading from the unadulterated sample.

There are a number of ways that signals arising at detectors from the addition of added analyte to the sample chamber can be used to adjust the signal from the unadulterated sample to improve the accuracy of the measurement. For example the unadulterated and adulterated samples can be considered to be discrete measurements where the adulterated sample contains a stable known amount of added analyte and this is used to correct the unadulterated signal. In this modality, the relationship between analyte level and measured signal may be different at the two time points, but this difference can be pre-characterised and used to accurately measure the intrinsic and total (intrinsic plus added) analyte levels at respective time points.

Alternatively, the rate of dissolution or diffusion of the analyte in the particular test sample matrix could be inferred by single measurement of a transient analyte level or by a series of measurements over time. This information could be used to apply a correction factor to the unadulterated sample, for example by reference to a 'lookup table' in the processor which contains information about the relationship between dissolution and/or diffusion rates and test sample measurement accuracy.

This latter method of adjustment may be used with a further development of the embodiments in which multiple discrete amounts of analyte are positioned in the detection chamber. These discrete amounts could be spatially separated throughout the chamber to provide a desired release profile or detection profile at the detector, or could be provided in a range of different formulations with, for example, differing time release profiles.

This method has the ability to correct for several error sources in test systems where the rate of diffusion to the detector is an important aspect of the correct functioning of the system. For example, in blood glucose monitoring, hematocrit levels and test temperatures both affect the diffusivity of glucose in blood and thereby inaccuracies can arise if there is deviation in hematocrit level or test temperature from the conditions under which the system has been calibrated.

Since this particular method of correction involves a step where properties of the test sample are inferred from measurement of diffusivity, it is possible that this information could additionally be used for other means. For example, a meter could keep a record of blood diffusivity as an indicator of haematocrit and/or plasma viscosity and determine if a person's hematocrit level is changing. This could be an early indicator of a change in a person's state of health. Alternatively, if the meter detected a significant (step) change in blood diffusivity, it could prompt the user to determine whether he or she is the normal user of that system. This can be a useful intervention because it could warn potential users of the cross contamination risks associated with using someone else's meter or the meter could store test data in a separate file, preventing any potential confusion arising from interpretation of trending data, or use different baseline configurations such as look up tables depending on the user.

In one embodiment of a method of the present invention, the internal calibration is achieved by incorporating a predetermined amount of glucose into the test sample and measuring the blood glucose response in both the presence and in the absence of the added glucose. The difference between the signal generated by the two samples is used to modify the unadulterated sample result.

An example situation is given below, in which the numbers have been chosen for purely illustrative purposes:

|  | Normal Haematocrit range (Hct) | High Hct | Low Hct |
| --- | --- | --- | --- |
| Unadulterated test result (mM) | 5 | 4 | 6 |
| Calibration result (mM) | 10 | 8 | 12 |
| Adjusted result (mM) | 5 | 5 | 5 |

The adjusted concentration result is obtained as:

$$Gl_{adj} = (Gl_{un} \times Q)/(G_{cal} - Gl_{un})$$

where $Gl_{adj}$, $Gl_{un}$ and $Gl_{cal}$ are respectively the adjusted analyte concentration, the analyte concentration measured in the unadulterated sample of the fluid, and the analyte concentration measured in the calibration sample and Q is the known increase in concentration of analyte in the calibration sample resulting from the addition of a known amount of the analyte to a known volume of sample.

In an alternative embodiment, the measurement of a level of added analyte can be used to infer a property of the test sample matrix and this knowledge can be used to correct the analyte sample level based on a known relationship between that property and error that it might cause. For example, a blood glucose monitor may determine a blood glucose reading of 6 mM, when the true, plasma referenced value is 5 mM, if the hematocrit level of the blood test sample is unexpectedly low at, say, 30%. Under these conditions, diffusion of added glucose to a detector may be faster than under conditions of normal hematocrit (usually 40-50%). Hence the rate of change of glucose concentration arising from the added glucose could be 2 mMs$^{-1}$ instead of 1 mMs$^{-1}$ expected under normal conditions. A known relationship between observed rate of change of glucose concentration from added glucose and hematocrit could reveal that the test sample has a hematocrit value of 30%. A further known relationship, between hematocrit and error causation could suggest that 30% hematocrit causes readings to be artificially raised by 20% and so this would enable the system to correct the erroneous reading of 6 mM to an accurate reading of 5 mM.

In this case, the level of calibration analyte measured could be a transient flux or concentration or a rate of change in flux or concentration. In this embodiment, it is possible that the calibration analyte and the target analyte are the same chemical species, or they may be different species.

These illustrations demonstrate how a source of error can be eliminated from blood glucose measurements by using the internal calibration approach. In the examples given, the unadulterated test result varies as a consequence of different Hct levels in the test blood, despite the fact that the true glucose concentration is 5 mM in all cases. However the effect of the Hot level can be determined either by observing the difference in measured concentrations between the unadulterated sam and the calibration sample, to which a known increase in concentration has been effected or by measuring a difference between observed and expected levels from the added analyte measurement. Once the extent of the interference arising from Hct has been gauged, it is a relatively straightforward matter to correct for this effect. This illustration uses Hot as an example source of error, but the same rationale applies to other interferences or sources of error.

Other, more complex, algorithms could be used to modify the test result. For example weightings could be given to the internal live addition calibration and batch calibration in the calculation of glucose concentrations, for example:

Calculated glucose concentration=(glucose concentration derived from batch calibration+adjusted glucose concentration derived from live calibration)/2.

It is also possible that the shape of the curve of measured signal over time ('the transient') will vary depending on the source of the error. For example, changes in temperature can affect both the rate of diffusion of analyte to the detector and the rate of reaction and signal generation at the surface, whilst hematocrit changes would primarily affect analyte diffusivity. In order to make an effective correction, it may therefore be desirable to understand the nature of the error source as well as the magnitude of the error and to use this knowledge to select an appropriate correction algorithm. This could be achieved by characterising features such as peak height, time to peak height, maximum gradient etc of transients for different error sources. Such features could be apparent in the unadulterated or adulterated sample measurements, or a combination thereof.

Typically the detection chambers 2, 2', 2" as shown in FIGS. 1, 2 and 3 above form part of a sensor strip which has a capillary fill mechanism and a capillary flow path from a receiving area where the fluid to be tested is placed to the detection chamber 2, 2', 2".

Connectors (not shown) from the detectors 6, 6', 6" are provided in all embodiments for connection of the device to a transducer (not shown) which converts the signals from the electrodes into readable results and applies the appropriate algorithm(s) to calibrate the results.

In all of the above embodiments, it may be desirable that the amount of analyte 4, 4', 4" used for the calibration sample is accurately and precisely known. In order to achieve this, any one of a number of techniques may be used to apply the analyte 4, 4', 4" to the device. The analyte could be applied either in a solution form (where it could be dissolved in either an organic or non-organic solvent) or as a solid, neat or in combination with other formulation ingredients. Examples of techniques for applying the analyte are: coating technologies (e.g. slot die, wire wound rod or spraying), printing technologies (e.g. slot-die coating, ink-jet, screen, gravure or flexographic printing), dispensing technologies (e.g. positive displacement, aspirate and dispense or piezoelectrically driven), metering of glucose-loaded beads, deposition of glucose onto a solid-phase substrate such as paper or string.

In some of the above embodiments it may also be important to accurately determine or know the location of the added analyte. This can be achieved by well know deposition or printing techniques, such as the use of drop on demand dispensing or gravure printing. Additionally, the location of the added analyte could be controlled by modifying the surface energy of the substrate onto which analyte is added. For example, a hydrophobic ring could be formed around the target area for the analyte dosing so the dosed analyte does not extend beyond that ring and dries in a predetermined location.

For the first embodiment above, it is also preferable that the calibration analyte 4 mixes quickly and repeatably with the fluid sample once the fluid comes into contact with the analyte. This can be achieved through the placement pattern of the analyte 4 in the detection chamber 6.

Adjusting the formulation of the added analyte solution deposited into the flow path can also increase the rate of dissolution. Formulating with fast dissolving substances that increase the viscosity of the coating or deposition solution is particularly advantageous, since it enables good control of coating or deposition. Polymers including pullulan, alginate, polyvinyl pyrrolidone, polyvinyl alcohol, polyethylene glycol, caboxymethyl cellulose, hydroxyethyl cellulose, hydroxypropyl methyl cellulose, polyacrylates and natural gums can be used for this purpose, possibly also in combination with a plasticizer such as polyethylene glycol and sorbitol and a surfactant such as Triton X-100. Particular techniques which may be applied are micronisation of the glucose powder, co-formulation into rapidly re-suspending hydrocolloids forming a membrane, co-formulation with ingredients generating effervescence when re-suspended or freeze-drying to form a high porosity stable crystalline structure.

In some of the above embodiments, it may be desirable to separate different zones within the flow path to prevent inadvertent mixing before sample addition. For example, where there is a detector optimised for a non-analyte dependent measurement (e.g. hematocrit) in addition to a detector optimised for analyte detection, the areas of the flow path could be effectively kept separate by covering different detection with a film forming agent of low friability, such as a pullulan film, possibly with added plasticizers and surfactants.

For all the above embodiments, it is preferable that the rate of arrival of added analyte at the detector is insensitive to normal deviations in the manufacturing processes used for making the consumable test strip. One way to minimise sensitivity to position or absolute amount of the added analyte is to dose the analyte onto the substrate used to form the lid or base of the flow path as a continuous line or series of small discrete dots forming a line orthogonal to the flow direction. Thus when the substrate containing the dosed analyte is formed into a flow path surface and strips are cut out, the amount of dosed analyte exposed to the test sample is proportional to the flow path width. In this way, tolerance issues that could arise when a single discrete dot of analyte is dispensed onto the substrate with the possibility that a proportion of this dot is outside the part of the substrate that forms part of the flow path are avoided. Equally, the analyte could be uniformly coated onto the surface of the substrate.

In addition to dosing the analyte in a line orthogonal to the flow direction or as a uniform coating, the shape of the detector used to measure added analyte levels can be optimised to reduce sensitivity to manufacturing deviations. For example, where the analyte is dosed in a line orthogonal to the intended flow, it will be advantageous to shape the working electrode part of the detector in the flow path such that it has a longer dimension in the same direction as the flow than it does across the flow path and to position it such that the longer dimension extends beyond the edges of where the analyte line is positioned. In this way, the measurement of the dosed analyte becomes tolerant to variations in both the position of the dosed analyte and the position of the detector.

The precise details of the construction and manufacture of sensor strips is well known in the art, and the present invention can be embodied in sensor strips which are made from a wide variety of materials and by a wide variety of methods.

One example of a sensor strip is described here, purely for illustrative purposes. The strip has overall dimensions of 30×10×2 mm. The substrate and cover defining the capillary flow path are comprised of a flexible plastic, and the capillary cover is adhered to the base substrate by means of a pressure sensitive adhesive. Electrode tracks are formed from conductive screen printing inks or from sputtered then etched metals and active electrodes are manufactured by screen printing or dispensing an enzyme solution (potentially including a redox mediator) onto an underlying conductive track. A counter electrode forms a circuit and this may have mediator and enzyme at least partially overlaid. Some systems have a separate reference electrode. Generally such products are single use disposable products.

The readings from the detector may be used to provide an analyte level reading. The live calibration using the measurement from the calibration sample or analyte may be applied directly to the unprocessed measurements from the detector measuring the analyte level (in the unadulterated sample in the first, second and third embodiments), or applied to an analyte level reading which has been derived from the unprocessed measurements.

For example, the sensor strip of an embodiment of the present invention may be connected to a transducer which produces analyte level readings from an electrical input from an enzyme electrode detector by applying a calibration curve. The reading obtained may then be adjusted and corrected depending on the measurement from the calibration sample.

Alternatively, the electrical signal from the enzyme electrode detector may be adjusted or corrected as a result of the measurement from the calibration sample or analyte to create a corrected electrical signal which is then used by a transducer or processor to produce a corrected analyte level reading, for example by applying a calibration curve.

Although some aspects of the above description have been made with specific references to the testing of glucose in blood, it will be clear to the person skilled in the art that the principles could be applied to other clinically relevant analytes such as indicators of cardiovascular, liver and kidney function (e.g. cholesterol, haemoglobin, electrolytes, metabolites), infectious agents (e.g. viruses, bacteria), disease state indicators (e.g. C-reactive protein, antibodies, cellular signalling factors, hormones) and therapeutic indicators (e.g antibiotics and drugs), which may be contained in other samples of biological origin such as cerebrospinal fluid, urine, sweat, tears, semen and saliva or derived therefrom.

Equally, sortie aspects of the above description have been described with specific reference to electrochemical detection systems, but the principles described are valid for other detection means.

We claim:

1. A method for testing, in a portable device, a level of a clinically relevant analyte in a fluid, the method including the steps of:
    guiding an unadulterated sample of the fluid to a detection chamber containing an electrode at a location in the detection chamber and a known amount of an analyte which is spatially removed from the electrode;
    measuring at said location, using the electrode, the clinically relevant analyte level in said unadulterated sample of the fluid at a first predetermined time after the arrival of the fluid in said detection chamber;
    measuring at said location, using the same electrode, an analyte level in a calibration sample of the fluid formed by mixing said unadulterated sample of the fluid with said known amount of said analyte at a second predetermined time after the arrival of the fluid in said detection chamber, the second predetermined time being later than said first predetermined time; and
    adjusting the clinically relevant analyte level measured in said unadulterated sample using the analyte level measured in said calibration sample.

2. A method according to claim 1 wherein said analyte in said known amount of analyte is the same as said clinically relevant analyte.

3. A method according to claim 1 further including the step of generating the clinically relevant analyte level reading from said adjusted clinically relevant analyte level, wherein said step of adjusting is carried out on an unprocessed measurement of the clinically relevant analyte level in the unadulterated sample.

4. A method according to claim 1 further including the step of generating the clinically relevant analyte level reading from the measurement of the clinically relevant analyte level in the unadulterated sample, wherein said step of adjusting is carried out on the clinically relevant analyte level reading.

5. A method according to claim 1 wherein the step of adjusting is performed by comparison with an expected relationship.

6. A method according to claim 1 further including the step of measuring at said location, using the electrode, the analyte level in one or more further calibration samples of said fluid at further predetermined times after the arrival of the fluid in said detection chamber, wherein the further times are later than said second predetermined time, and wherein the step of adjusting uses all measured analyte levels.

7. A method according to claim 1 further including the step of releasing said predetermined amount of analyte into the detection chamber for mixing with said fluid in said chamber.

8. A method according to claim 1 wherein the sample of fluid which is guided to the detection chamber contains a known amount of said clinically relevant analyte, and further including the step of determining the condition of the portable device based on said measurements.

9. A method according to claim 1 further including a step of storing non-analyte specific information from the clinically relevant and calibration sample analyte levels measured.

10. A method according to claim 9 further including the steps of: storing a record of said non-analyte specific information; updating said record after subsequent measurements; and determining a deviation from said record in a subsequent measurement.

11. A method according to claim 10 further including the step of, if said deviation is greater than a predetermined amount, alerting the user.

12. A method according to claim 1 further including the steps of: recording said measured clinically relevant and calibration sample analyte levels for a predetermined length of time; analysing the shape of the measured clinically relevant and calibration sample analyte levels over said predetermined length of time; and selecting, based on said analysis, a correction algorithm from a plurality of such algorithms, to be used in said step of adjusting.

13. A method according to claim 12 wherein the step of analysing the shape of the measured clinically relevant and calibration sample analyte levels analyses one or more of the following features of the measured clinically relevant and calibration sample analyte levels: absolute value of the measured parameter, peak height, time to peak height, and maximum gradient of transients for different error sources.

* * * * *